United States Patent [19]

Lewis

[11] Patent Number: 4,705,765

[45] Date of Patent: Nov. 10, 1987

[54] HYDROSILYLATION CATALYST, METHOD FOR MAKING AND USE

[75] Inventor: Larry N. Lewis, Scotia, N.Y.

[73] Assignee: General Electric Company, Schenectady, N.Y.

[21] Appl. No.: 21,037

[22] Filed: Mar. 2, 1987

Related U.S. Application Data

[63] Continuation of Ser. No. 810,629, Dec. 19, 1985, abandoned.

[51] Int. Cl.$^4$ .................... B01J 31/00; C07F 7/04; C08G 77/06
[52] U.S. Cl. .................... 502/152; 502/158; 502/161; 502/162; 502/167; 556/438; 556/10; 528/15
[58] Field of Search ............... 502/152, 158, 161, 162, 502/167

[56] References Cited

U.S. PATENT DOCUMENTS

| | | | |
|---|---|---|---|
| 3,159,601 | 12/1964 | Ashby | 528/15 |
| 3,220,972 | 11/1965 | Lamoreaux | 528/27 X |
| 3,328,378 | 6/1967 | Piekarski et al. | 502/158 X |
| 3,336,239 | 8/1967 | Bailey et al. | 502/158 |
| 3,576,027 | 4/1971 | Fish | 556/439 |
| 3,715,334 | 2/1973 | Karstedt | 528/26 X |
| 3,775,452 | 11/1973 | Karstedt | 556/10 |
| 3,856,837 | 12/1974 | Chandra | 502/158 X |
| 3,907,850 | 9/1975 | Copka et al. | 502/167 X |
| 3,925,434 | 12/1975 | Chuang | 502/167 X |
| 4,292,434 | 9/1981 | Lindner et al. | 502/167 X |

FOREIGN PATENT DOCUMENTS 602218  5/1976  U.S.S.R. .................. 502/158

*Primary Examiner*—Andrew Metz
*Assistant Examiner*—William G. Wright
*Attorney, Agent, or Firm*—William A. Teoli; James C. Davis, Jr.; James Magee, Jr.

[57] ABSTRACT

A colloidal hydrosilylation catalyst is provided by effecting reaction between a silicon hydride or a siloxane hydride and a Pt(O) or Pt(II) catalyst. The colloidal catalyst forms stable mixtures with olefinically unsaturated organopolysiloxanes.

6 Claims, No Drawings

HYDROSILYLATION CATALYST, METHOD FOR MAKING AND USE

BACKGROUND OF THE INVENTION

This is a continuation of copending application Ser. No. 810,629, filed Dec. 19, 1985 now abandoned assigned to the same assignee as the present invention, and is incorporated herein by reference.

Prior to the present invention, various platinum catalysts were available for effecting the addition of silicon hydride to vinyl-substituted silicon materials referred to as "hydrosilylation". For example, Karstedt, U.S. Pat. Nos. 3,715,334 and 3,775,452 assigned to the same assignee as the present invention, shows the use of Pt(O) complex with vinylsilicon siloxane ligands as an active hydrosilylation catalyst. Additional platinum complexes, such as complexes with platinum halides are shown by Ashby, U.S. Pat. No. 3,159,601 and Lamoreaux, U.S. Pat. No. 3,220,972, assigned to the same assignee as the present invention.

Another hydrosilylation catalyst is shown by Fish, U.S. Pat. No. 3,576,027. Fish prepares a platinum(IV) catalyst by reacting crystalline platinum(IV) chloroplatinic acid and organic silane or siloxane to form a stable reactive platinum hydrosilylation catalyst.

Although the aforementioned patents show that various platinum complexes are efficient hydrosilylation catalysts, additional platinum complexes providing improved hydrosilylation rates are constantly being sought.

The present invention is based on my discovery that a colloidal platinum complex in the form of a reaction product of a silicon hydride and an organic solvent solution of a platinum(O) complex or a platinum(II) complex, can provide superior hydrosilylation rates. I have found that in particular instances, optimum catalyst activity can be obtained, if the components of the reaction mixture are allowed to react for a time sufficient to provide a colloid having a red to a red-brown or black color.

STATEMENT OF THE INVENTION

There is provided by the present invention a colloidal hydrosilylation catalyst comprising
(A) the reaction product of
 (i) a silicon hydride or siloxane hydride, and (ii) a platinum(O) or platinum(II) complex, and
(B) 2 to 20 parts by weight of aprotic solvent per part of (A).
where there is utilized in (A) 6 to 50 moles of ≡SiH in (i), per mole of Pt in (ii).

Some of the platinum Pt(O) and Pt(II) complexes which can be utilized in the practice of the present invention can have at least one ligand selected from the class consisting of halides, $C_{(1-8)}$ alkyl radicals, $C_{(6-14)}$ aryl radicals, $C_{(1-8)}$ aliphatically unsaturated organic radicals, nitriles and carbon monoxide. Some of these platinum complexes are for example:

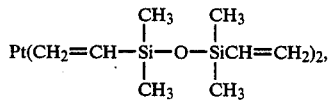

$(C_8H_{12})_2Pt$, $C_8H_{12}$ = 1,5-cyclooctadiene, $(C_8H_{12})PtCl_2$, $[(C_2H_4)PtCl_2]_2$, $PtCl_2(CO)_2$, $PtCl_2(CH_3CN)_2$, -continued
$(C_8H_{12})Pt(C_6H_5)_2$, and $(C_8H_{12})Pt(CH_3)_2$.

Some of the silicon hydride or siloxane hydride which can be utilized in the practice of the present invention are, for example:

$(C_2H_5O)_3SiH$, $(C_2H_5)_3SiH$, $[(CH_3)_3SiO]_2Si(H)CH_3$,

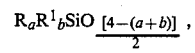, $Cl_2(CH_3)SiH$, and $(CH_3)_2C_6H_5SiH$.

In the practice of the present invention, the platinum colloid catalyst, hereinafter referred to as the colloid catalyst, can be prepared by initially dissolving platinum(O) complex or platinum(II) complex in an aprotic organic solvent such as methylene chloride, tetrahydrofuran, benzene, xylene, toluene, and diethylether. The solution of the platinum complex having from about 1 to 10 percent by weight of platinum, can be mixed with the silicon hydride at temperatures in the range of from −10° C. to 40° C. Generally, there is an induction period of from one minute to two hours after which time a reaction between the silicon hydride and the platinum complex occurs as shown by the liberation of hydrogen gas. In addition, a colored reaction product can form which initially can be yellow and eventually turn to a red, reddish brown or burgandy color. The resulting colloid can have platinum particles having an average diameter of 30 Angstroms to 700 Angstroms.

In another aspect of the present invention, the colloid catalyst can be incorporated into olefinically unsaturated organopolysiloxane as shown by the formula $$R_aR^1_bSiO_{\frac{[4-(a+b)]}{2}},$$

where R is a member selected from the class consisting of $C_{(1-14)}$ monovalent hydrocarbon radicals and substituted $C_{(1-14)}$ monovalent hydrocarbon radicals, $R^1$ is a $C_{(1-10)}$ olefinically unsaturated aliphatic radical, a is a whole number having a value of 0 to 3 inclusive and preferably a has an average value of from 0.5 to 2 inclusive, b has an average value of 0.005 to 2.0 inclusive and the sum of a and b is equal to from 0.8 to 3 inclusive. The resulting mixture which is stable at ambient temperature over an extended shelf period can have 5 to 200 ppm of platinum.

The above olefinically unsaturated organopolysiloxanes include fluid organopolysiloxanes which preferably are free of silanic hydrogen, and contain olefinic unsaturation by means of double bonds between two adjacent aliphatic carbon atoms. Among the radicals which R represents are included alkyl, such as methyl, ethyl, propyl, isopropyl, butyl, octyl, dodecyl, and the like, cycloalkyl, such as cyclopentyl, cyclohexyl, cycloheptyl, and the like, aryl such as phenyl, naphthyl, tolyl, xylyl, and the like, aralkyl, such as benzyl, phenylethyl, phenylpropyl, and the like; halogenated derivatives of the aforesaid radicals including chloromethyl, trifluoromethyl, chloropropyl, chlorophenyl, dibromophenyl, tetrachlorophenyl, difluorophenyl, and the like; cyanoalkyl, such as beta-cyano ethyl, gamma-cyanopropyl, beta-cyanopropyl and the like. Preferably R is methyl. Moreover, R is intended to include materials where R is a mixture of the aforesaid radicals.

Among the radicals represented by $R^1$ there are included alkenyl, such as vinyl, allyl, methallyl, butenyl, pentyl, and the like. Preferably, $R^1$ is vinyl or allyl and most preferably $R^1$ is vinyl.

The above olefinically unsaturated organopolysiloxanes are well known in the art, as particularly manifested by U.S. Pat. No. 3,344,111 to Chalk, and U.S. Pat. No. 3,436,366 to Modic, which are incorporated herein by reference. Similarly, their preparation and/or commercial availability is also well known.

Specific materials included within the scope of the olefinically unsaturated organopolysiloxanes are low molecular weight materials, such as vinylpentamethyldisiloxane, 1,3-divinyltetramethyldisiloxane, 1,1,3-trivinyltrimethyldisiloxane, 1,1,3,3-tetravinyldimethyldisiloxane, as well as higher polymers containing up to 100,000 or more silicon atoms per molecule. Also included within the scope of the olefinically unsaturated organopolysiloxanes are cyclic materials containing silicon-bonded vinyl or allyl radicals, such as the cyclic trimer, tetramer or pentamer of methylvinylsiloxane $$((CH_2=CH)(CH_3)SiO)$$

or methyl allylsiloxane $$((CH_2=CH-CH_2)(CH_3)SiO).$$

Among these cyclic materials, tetramethyltetraallylcyclotetrasiloxane and tetramethyltetravinylcyclotetrasiloxane are preferred.

A preferred class of vinylorganopolysiloxane which can be used in the practice of the present invention are those shown by Modic in U.S. Pat. No. 3,436,366, incorporated herein by reference. These compositions comprise (1) 100 parts by weight of a liquid vinyl chain-stopped polysiloxane having the formula

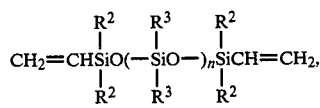

wherein $R^2$ and $R^3$ are monovalent hydrocarbon radicals free of aliphatic unsaturation, with at least 50 mole percent of the $R^3$ groups being methyl, and where n has a value sufficient to provide a viscosity of from about 50,000 to 750,000 centistokes at 25° C., preferably from about 50,000 to 180,000 and (2) from 20 to 50 parts by weight of an organopolysiloxane copolymer comprising $(R^4)_3SiO_{0.5}$ units and $SiO_2$ units, where $R^4$ is a member selected from the class consisting of vinyl radicals and monovalent hydrocarbon radicals free of aliphatic unsaturation, where the ratio of $(R^4)_3SiO_{0.5}$ units to $SiO_2$ units is from about 0.5:1 to 1:1, and where from about 2.5 to 10 mole percent of the silicon atoms contain silicon-bonded vinyl groups.

The vinyl chain-stopped organopolysiloxane component is typified by various compositions where the monovalent hydrocarbon radicals represented by $R^2$ and $R^3$ include alkyl radicals, e.g., methyl, ethyl, propyl, butyl, octyl, etc.; aryl radicals, e.g., phenyl, tolyl, xylyl, etc.; cycloalkyl radicals, e.g., cyclohexyl, cyclohepthyl, etc.; aralkyl radicals, e.g., benzyl, phenylethyl, etc. Preferably, all of the radicals represented by $R^2$ and $R^3$ are selected from the group consisting of methyl and phenyl radicals and most preferably $R^2$ and $R^3$ are methyl. In the organopolysiloxane copolymer component $R^4$ can be vinyl and/or monovalent hydrocarbon radicals free of aliphatic unsaturation, with at least the stated proportion of $R^4$ groups being vinyl. The $r^4$ groups which are not vinyl can be selected from $R^2$ and $R^3$ groups and are preferably methyl.

The silicon hydride previously described includes organohydrogenpolysiloxanes are intended to broadly cover fluid organopolysiloxanes which are preferably free of olefinic unsaturation and which contain silanic hydrogen. These organohydrogenpolysiloxanes are also well known in the art as shown by U.S. Pat. No. 3,344,111 to Chalk, and U.S. Pat. No. 3,436,366, incorporated herein by reference.

Additional silicon hydride or siloxane hydride include 1,3-dimethyldisiloxane, 1,1,3,3-tetramethyldisiloxane, as well as higher polymers containing up to 100,000 or more silicon atoms per molecule. Also included within are cyclic materials, such as cyclic polymers of methyl hydrogen siloxane having the formula

where x is a whole number equal to from 3 to 10 and preferably 3 or 4 such as tetramethylcyclotetrasiloxane.

Siloxane hydride also can include siloxane units such as hydrogen siloxane units $(H_2SiO)_{1.5}$, methyl hydrogen siloxane units $CH_3(H)SiO$, dimethyl hydrogen siloxane units, and dihydrogen siloxane units $(H_2SiO)$. These copolymers can contain from 0.5 to 99.5 mole percent of $(R)_aSiO$ units chemically combined with 0.5 to 99.5 mole percent of siloxy units having at least one hydrogen including a mixture of hydrogen and R radicals attached to silicon.

The following examples are given by way of illustration and not by way of limitation. All parts are by weight.

EXAMPLE 1

There was added 50 microliters of triethoxysilane to 0.1 ml of a xylene solution of a platinum vinyl disiloxane catalyst (Karstedt) having 5% by weight of platinum. The resulting mixture had a 10 molar excess of the silane. An exothermic reaction occurred within 15 minutes at 25° C. The resulting clear solution which was initially orange turned black. Based on method of preparation, there was obtained a platinum colloid catalyst having about 3% by weight of platinum and an average particle size of about 40 Angstroms. The solution was stored in a freezer at −20° C.

There was combined 6 grams of a dimethyl vinylsiloxy end stopped methylvinylsiloxane having an average of 1.65 wt % of vinyl attached to silicon and a viscosity of 500 centipoise at 25° C., 0.67 gram of a silicon hydride siloxane having 0.8 wt % hydrogen and 50 centipoise viscosity and 10 ppm of platinum hydrosilylation catalyst. The hydrosilylation catalyst utilized was either the above platinum vinyldisiloxane (Karstedt) or the platinum colloid catalyst of the present invention (Colloid). The following results were obtained where the gel time was based on an average of 3 measurements at 25° C.

|  | Karstedt | Colloid |
|---|---|---|
| Time to Gel (min) | 21.1 | 8.5 |

These results show that the colloid catalyst of the present invention is superior to the platinum(O) catalyst of the prior art.

EXAMPLE 2

A mixture of 6 grams of a vinyl siloxane oil having a viscosity of 400 centipoise at 25° C. and chain terminated with dimethylvinylsiloxy units and 10 ppm platinum colloid catalyst of Example 1 was stored at 25° C. for 3 months. A gel time was measured by adding 1 part of a silicon hydride crosslinker to 9 parts of the platinum containing vinyl silicon oil. It was found that no loss in activity was observed as compared to the results shown in Example 1.

Mixtures were made by incorporating 10 ppm platinum of the above colloid catalyst and several 6 gram samples of the vinyl silicon oil of Example 1. These mixtures were stored at 60° C. for 35 days. A silicon hydride crosslinker was added to the platinum containing vinyl silicon oils and the resulting mixtures were found to gel at 1.2 minutes. The same procedure was repeated except that 10 ppm of the Karstedt catalyst was employed. A gel time of 2.1 minutes was obtained.

These results show that the platinum colloid catalyst of the present invention can be used to form stable mixtures of vinyl silicon oil exhibiting superior gel times after a substantial shelf period at ambient temperatures and above as compared to the platinum catalyst of the prior art.

EXAMPLE 3

A heat curable mixture was prepared by blending 10 ppm of platinum of platinum colloid catalyst of Example 1, into 100 parts of a vinyl containing polydimethylsiloxane gum reinforced with 35 parts hexamethyldisilazane treated silica filler, and 10 parts of a methyl hydrogen siloxane fluid having an average of 0.9% by weight of hydrogen and a 20 centipoise viscosity at 25° C. The various ingredients were stirred together, placed in a mold and then subjected to 10 tons of pressure at 126° C. for 45 minutes. There was obtained a cured silicon rubber having a hardness (Shore A) of 34 and elongation (percent) of 536 and a tensile strength (psi) of 753. These properties are substantially better than the corresponding silicone rubber made by following the same procedure utilizing the above prior art Karstedt catalyst of Example 1. Accordingly, there was obtained an elongation (percent) of 504, and a tensile strength (psi) of 637.

EXAMPLE 4

There was added 0.2 ml of triethoxysilane to 2 ml of a methylenechloride solution of 0.06 gram of a cyclooctadiene platinum dichloride complex. The resulting mixture turned yellow in one hour, then red in two hours. Hydrogen was continuously evolved during the two-hour period. Based on method of preparation, there was obtained a colloid platinum catalyst solution containing about 1% by weight of platinum having an average particle size of 30 Angstroms.

There was added 10 parts per million of platinum catalyst to a mixture of 6 grams of a polydimethylsiloxane fluid terminated with dimethylvinylsiloxy units and having an average of 3 mole % of chemically combined vinylsiloxy units and a viscosity of 400 centipoises and 0.67 grams of a methyl hydrogen siloxane fluid having an average of 0.8% by weight of hydrogen attached to silicon and consisting essentially of chemically combined methyl hydrogen siloxy units and dimethylsiloxy units in a viscosity of 50 centipoise at 25° C. The following results were obtained at 25° C. where "Colloid" is the platinum catalyst of the present invention and CODPtCl$_2$ is the cyclooctadiene platinum dichloride catalyst of the prior art.

|  | Colloid | CODPtCl$_2$ |
| --- | --- | --- |
| Gel Time (min) | 29.5 | 121 |

The above results show that the colloid catalyst of the present invention is superior to the prior art cyclooctadiene platinum dichloride catalyst. It was further found that unless the platinum colloid catalyst of the present invention is maintained at −20° C., it can suffer degradation in catalyst activity after a period of about five days at ambient temperature.

EXAMPLE 5

A comparison was made between the activity of the colloid catalyst prepared in accordance with Example 1 and the platinum catalyst shown by Example 1 of Fish, U.S. Pat. No. 3,576,027. In accordance with Fish's teaching, a few crystals of chloroplatinic acid (0.0298 g, 39% PT, H$_2$PtCl$_6$·xH$_2$O) were added to a reaction vessel and 1.1 g of methyldichlorosilane was poured over the crystals in the vessel. The reaction occurred under a nitrogen atmosphere which resulted in the evolution of gas. The mixture turned a pale yellow color after about three hours at ambient temperatures. After five hours, gas evolution ceased.

10 parts per million of platinum catalyst was added to a hydrosilylation mixture of 1 part of triethoxysilane and 1 part of trimethylvinylsilane. It was found that the catalyst of Example 1 "Colloid" effected a 100% conversion of the hydrosilylation mixture, in less then five minutes. It was found that the Fish catalyst resulted in less than 5% conversion after about eight hours, while use of a chloroplatinic acid isopropanol catalyst resulted in almost quantitative conversion in about eight hours.

An additional evaluation was made with the Fish catalyst which was allowed to rest for two days after initial preparation at 25°. It turned a deep red color. It was found that after about 90 minutes, an 80% conversion of the above hydrosilylation mixture was obtained. A possible explanation for the reduced activity of the Fish catalyst as compared to the colloid catalyst of the present invention is that the Fish catalyst is derived from a platinum(IV) complex such as chloroplatinic acid, and not a platinum(O) or platinum(II) complex. This shows that colloids formed from a Pt(O) or Pt(II) complex can provide enhanced hydrosilylation activity as compared to the platinum catalyst of the prior art.

Although the above examples are directed to only a few of the very many variables which can be employed in the practice of the present invention, it should be understood that the present invention is directed to the use of a much broader variety of platinum(O) and platinum(II) catalysts as well as silicon hydride utilized in forming such colloid platinum colloid catalyst.

What is claimed and sought to be protected by Letters Patent of the United States is as follows:

1. A colloidal hydrosilylation catalyst comprising,
    (A) the reaction product of
        (i) a silicon hydride or siloxane hydride, and
        (ii) a platinum Pt(O) or Pt(II) complex, and
    (B) 2 to 20 parts by weight of aprotic solvent, per part of (A), where there is utilized in (A), 6 to 50 moles of ≡SiH in (i), per mole of Pt in (ii).

2. The colloid catalyst in accordance with claim 1, resulting from the reaction of a platinum(O) complex with a silicon hydride or siloxane hydride.

3. The colloid catalyst in accordance with claim 1, resulting from the reaction of a silicon hydride or siloxane hydride with a platinum(II) complex.

4. A colloid complex in accordance with claim 1, resulting from the reaction of a platinum(O) complex with a silicon hydride or siloxane hydride having vinyl siloxane ligands.

5. A mixture comprising an olefinically unsaturated organopolysiloxane having the formula, $$R_a R^1_b SiO_{\frac{[4-(a+b)]}{2}}$$

and 5 parts per million to 200 parts per million of platinum in the form of colloidal hydrosilylation catalyst comprising, (A) the reaction product of
  (i) a silicon hydride or siloxane hydride,
  (ii) a platinum Pt(O) or Pt(II) complex, and
(B) 2 to 20 parts by weight of aprotic solvent, per part of (A), where R is a member selected from the class consisting of $C_{(1-14)}$ monovalent hydrocarbon radicals and substituted $C_{(1-14)}$ monovalent hydrocarbon radicals, $R^1$ is a $C_{(1-10)}$ olefinically unsaturated aliphatic radical, a is a whole number having a value of 0 to 3 inclusive and b has an average value of 0.005 to 2.0 inclusive.

6. A mixture in accordance with claim 5, comprising a vinyl siloxane and 5 parts per million to 200 parts per million of platinum in the form of a colloid catalyst comprising a colloidal hydrosilylation catalyst comprising:

(A) the reaction product of
  (i) a silicon hydride or siloxane hydride, and
  (ii) from 6 to 50 moles of ≡SiH of (i) per mole of platinum in a Pt(O) or Pt(II) complex of at least one ligand selected from a member of the class consisting of phosphines, halides, $C_{(1-8)}$ alkyl radicals, $C_{(6-14)}$ aryl radicals, $C_{(1-8)}$ aliphatically unsaturated organic radicals, cyanide and carbon monoxide, and
(B) 2 to 20 parts by weight of aprotic solvent per part of (A).

* * * * *